(12) United States Patent
Kuroda et al.

(10) Patent No.: US 10,006,843 B2
(45) Date of Patent: Jun. 26, 2018

(54) METHOD FOR PREDICTING REMAINING LIFE OF HOSE AND METHOD FOR DIAGNOSING DETERIORATION LEVEL OF HOSE

(71) Applicant: BRIDGESTONE CORPORATION, Tokyo (JP)

(72) Inventors: Taisuke Kuroda, Yokohama (JP); Kouji Suzuki, Hayama-machi (JP); Yoshikatsu Sakai, Saitama (JP)

(73) Assignee: BRIDGESTONE CORPORATION, Tokyo (JP)

( * ) Notice: Subject to any disclaimer, the term of this patent is extended or adjusted under 35 U.S.C. 154(b) by 0 days. days.

(21) Appl. No.: 15/126,016

(22) PCT Filed: Mar. 19, 2015

(86) PCT No.: PCT/JP2015/001555
§ 371 (c)(1),
(2) Date: Sep. 14, 2016

(87) PCT Pub. No.: WO2015/141232
PCT Pub. Date: Sep. 24, 2015

(65) Prior Publication Data
US 2017/0082526 A1  Mar. 23, 2017

(30) Foreign Application Priority Data
Mar. 19, 2014 (JP) .................. 2014-056931

(51) Int. Cl.
*G01N 3/20* (2006.01)
*G01M 5/00* (2006.01)

(52) U.S. Cl.
CPC ............. *G01N 3/20* (2013.01); *G01M 5/0025* (2013.01); *G01M 5/0033* (2013.01);
(Continued)

(58) Field of Classification Search
CPC ... G01N 2203/0023; G01N 2203/0274; G01N 2203/0073; G01N 2203/028;
(Continued)

(56) References Cited

U.S. PATENT DOCUMENTS 3,621,711 A * 11/1971 Funk et al. .............. G01N 3/34
                                                              73/794
5,287,757 A *  2/1994 Polaert ................ G01G 3/1402
                                                             177/211
(Continued)

FOREIGN PATENT DOCUMENTS

CN    103471933 A    12/2013
JP    2-108940 A     4/1990
(Continued)

OTHER PUBLICATIONS

International Search Report of PCT/JP2015/001555 dated Jun. 9, 2015 [PCT/ISA/210].
(Continued)

*Primary Examiner* — Jonathan Dunlap
(74) *Attorney, Agent, or Firm* — Sughrue Mion, PLLC (57) ABSTRACT

Provided is a method for predicting the remaining life of a hose and a method for diagnosing the deterioration level of a hose that can be easily performed without breaking the hose. The disclosure includes: a testing step of performing a hose bending test; and a predicting step of predicting the remaining life of a hose subject to prediction, wherein during the hose bending test, either a value of an external force required to displace a hose portion in a direction of the external force by a predetermined displacement amount, or a value of a displacement amount in a direction of the external force of the hose portion when the external force of
(Continued)

a predetermined magnitude is exerted on the hose portion is measured, and the measured value is obtained as the test result.

12 Claims, 4 Drawing Sheets

(52) U.S. Cl.
CPC ........ *G01M 5/0058* (2013.01); *G01M 5/0075* (2013.01); *G01N 2203/0023* (2013.01); *G01N 2203/0073* (2013.01); *G01N 2203/028* (2013.01); *G01N 2203/0266* (2013.01); *G01N 2203/0274* (2013.01)

(58) Field of Classification Search
CPC ............ G01N 2203/0266; G01N 3/20; G01M 5/0025; G01M 5/0033; G01M 5/0075; G01M 5/0058
USPC .................................. 73/849, 812, 856, 829
See application file for complete search history.

(56) References Cited

U.S. PATENT DOCUMENTS

| | | | | |
|---|---|---|---|---|
| 6,076,411 A * | 6/2000 | Horvath | ................. | G01N 21/88 73/865.8 |
| 7,561,976 B2 * | 7/2009 | Bernard | ................. | G01H 13/00 33/550 |
| 7,770,467 B1 * | 8/2010 | Halderman | .............. | G01N 3/04 73/849 |
| 8,006,568 B2 * | 8/2011 | Halderman | .............. | G01N 3/04 73/818 |
| 8,544,339 B2 * | 10/2013 | McKee | ................... | E21B 19/22 73/829 |
| 9,038,478 B2 * | 5/2015 | Hovhanessian | .......... | G01N 3/32 73/789 |
| 2002/0108449 A1 * | 8/2002 | Kohli | .................. | G01M 5/0025 73/849 |
| 2006/0288770 A1 * | 12/2006 | Nowack | .................. | B63B 21/00 73/158 |
| 2010/0174495 A1 * | 7/2010 | Pereira | .................. | F16L 11/127 702/34 |
| 2010/0251838 A1 * | 10/2010 | Halderman | .............. | G01N 3/04 73/866.5 |
| 2011/0036148 A1 * | 2/2011 | Stubler | ................. | G01M 3/005 73/40.5 R |
| 2011/0154908 A1 * | 6/2011 | Mckee | .................... | E21B 19/22 73/829 |
| 2014/0190268 A1 * | 7/2014 | Hovhanessian | .......... | G01N 3/32 73/812 |
| 2016/0003723 A1 * | 1/2016 | Chapman | ................. | G01N 3/26 73/37 |

FOREIGN PATENT DOCUMENTS

| | | |
|---|---|---|
| JP | 0690196 B2 | 11/1994 |
| JP | 2004-271414 A | 9/2004 |
| JP | 2007-263908 A | 10/2007 |

OTHER PUBLICATIONS

Written Opinion of PCT/JP2015/001555 dated Jun. 9, 2015 [PCT/ISA/237].
Communication dated Apr. 25, 2018, from the State Intellectual Property Office of People's Republic of China in counterpart Application No. 201580014909.5.

* cited by examiner

METHOD FOR PREDICTING REMAINING LIFE OF HOSE AND METHOD FOR DIAGNOSING DETERIORATION LEVEL OF HOSE

CROSS REFERENCE TO RELATED APPLICATIONS

This application is a National Stage of International Application No. PCT/JP2015/001555, filed Mar. 19, 2015, claiming priority based on Japanese Patent Application No. 2014-056931, filed Mar. 19, 2014, the contents of all of which are incorporated herein by reference in their entirety.

TECHNICAL FIELD

The disclosure relates to a method for predicting the remaining life of a hose and a method for diagnosing the deterioration level of a hose.

BACKGROUND

Generally, hoses having a rubber layer on the inner peripheral side are sometimes used for transmitting a high-temperature, high-pressure fluid (oil and the like) in construction machines, plant facilities and the like. Even if such hoses are used within the appropriate ranges set for their specifications, long term use of the hoses leads to gradual thermal aging of the rubber layer on the inner peripheral side due to the heat of the fluid. When excessive thermal aging of the rubber layer on the inner peripheral side is caused, there may be problems such as leaking of the fluid inside the hose from between the joint and the hose. To prevent such problems, it is effective to predict the remaining life of the hose or to diagnose the deterioration level of the hose on a regular basis to prevent the use of a hose with an excessively deteriorated rubber layer.

An example of a method for predicting the remaining life of the hose or diagnosing the deterioration level of the hose is a method of cutting out a part of the rubber layer on the inner peripheral side, measuring its physical properties, and using the results thereof. Further, proposed in JP2004271414A (PTL 1) is a method of attaching, to the base cap of the end of the hose, a rubber body for confirming deterioration which is made of the same material as the inner rubber layer of the hose in a state of being stretched by a predetermined amount, observing the rubber body for confirming deterioration from the outside to estimate the deterioration state of the inner rubber layer and detect hose deterioration.

CITATION LIST

Patent Literature

PTL 1: JP2004271414A

SUMMARY

Technical Problem

However, with the method of predicting the remaining life of the hose or diagnosing the deterioration level of the hose by cutting out a part of the rubber layer, it is necessary to break the hose, and there are problems such as that the use of the hose is suspended, or the results cannot be immediately obtained at the use site. Further, with the method described in PTL1, there is a problem in that the costs and number of steps increase since it is necessary to provide a rubber body for confirming the deterioration as a component other than the hose.

It could therefore be helpful to provide a method for predicting the remaining life of a hose and method for diagnosing the deterioration level of a hose that can be easily performed without breaking the hose.

Solution to Problem

The method for predicting remaining life of a hose described herein is a method for predicting remaining life of a hose having a metal wire layer and an inner tube rubber layer disposed on an inner peripheral side of the metal wire layer, the method comprising: a testing step of performing a hose bending test on a hose subject to prediction for remaining life; and a predicting step of predicting remaining life of the hose subject to prediction based on comparison between a test result obtained by performing the hose bending test on the hose subject to prediction and a test result obtained by performing the hose bending test beforehand on a hose of the same type which is in a use limit state, wherein during the hose bending test, while an external force is exerted on a predetermined hose portion of a hose subject to testing to cause bending deformation in the hose portion, either a value of the external force required to displace the hose portion in a direction of the external force by a predetermined displacement amount, or a value of a displacement amount in a direction of the external force of the hose portion of when the external force of a predetermined magnitude is exerted on the hose portion is measured, and the measured value is obtained as the test result.

According to the method for predicting remaining life of a hose described herein, it is possible to easily perform remaining life prediction of a hose without breaking the hose.

In the method for predicting remaining life of a hose described herein, it is preferable that, during the hose bending test, while exerting the external force on the hose portion, the hose is supported from a direction opposite to the direction of the external force at predetermined supporting positions on both sides of the hose portion in an extending direction of the hose.

This way, the difference in the test results according to the deterioration level of the hose appears more clearly.

In the method for predicting remaining life of a hose described herein, a distance between the predetermined supporting positions is preferably 150 mm or less.

This way, the hose bending test can be performed more easily.

In the method for predicting remaining life of a hose described herein, the predetermined displacement amount is preferably 20 mm or less.

This way, the hose bending test can be performed more easily and the load on the hose can be suppressed.

In the method for predicting remaining life of a hose described herein, the hose may have an outermost layer coated with a protective cover.

Even in such case, the hose bending test can be performed with sufficient accuracy, and therefore the convenience for the user is improved.

The method for diagnosing deterioration level of a hose described herein is a method for diagnosing deterioration level of a hose having a metal wire layer and an inner tube rubber layer disposed on an inner peripheral side of the metal wire layer, the method comprising: a testing step of performing a hose bending test on a hose subject to diagnosis for deterioration level; and a diagnosing step of diagnosing deterioration level of the hose subject to diagnosis based on comparison between a test result obtained by performing the hose bending test on the hose subject to diagnosis and a test result obtained by performing the hose bending test beforehand on a hose of the same type as the hose subject to diagnosis and of a known total usage time, wherein during the hose bending test, while an external force is exerted on a predetermined hose portion of a hose subject to testing to cause bending deformation in the hose portion, either a value of the external force required to displace the hose portion in a direction of the external force by a predetermined displacement amount, or a value of the displacement amount in a direction of the external force of the hose portion of when the external force of a predetermined magnitude is exerted on the hose portion is measured, and the measured value is obtained as the test result.

According to the method for diagnosing deterioration level of a hose described herein, it is possible to easily perform deterioration diagnosis of a hose without breaking the hose.

In the method for diagnosing deterioration level of a hose described herein, it is preferable that, in the hose bending test, while exerting the external force on the hose portion, the hose is supported from a direction opposite to the direction of the external force at predetermined supporting positions on both sides of the hose portion in an extending direction of the hose.

This way, the difference in the test results according to the deterioration level of the hose appears more clearly.

In the method for diagnosing deterioration level of a hose described herein, a distance between the predetermined supporting positions is preferably 150 mm or less.

This way, the hose bending test can be performed more easily.

In the method for diagnosing deterioration level of a hose described herein, the predetermined displacement amount is preferably 20 mm or less.

This way, the hose bending test can be performed more easily and the load on the hose can be suppressed.

In the method for diagnosing deterioration level of a hose described herein, the hose may have an outermost layer coated with a protective cover.

Even in such case, the hose bending test can be performed with sufficient accuracy and therefore the convenience for the user is improved.

Advantageous Effect

According to the disclosure, it is possible to provide a method for predicting the remaining life of a hose and a method for diagnosing the deterioration level of a hose that can be easily performed without breaking the hose.

DETAILED DESCRIPTION

An embodiment of the disclosure will be demonstratively described with reference to the drawings.

Figure 1:
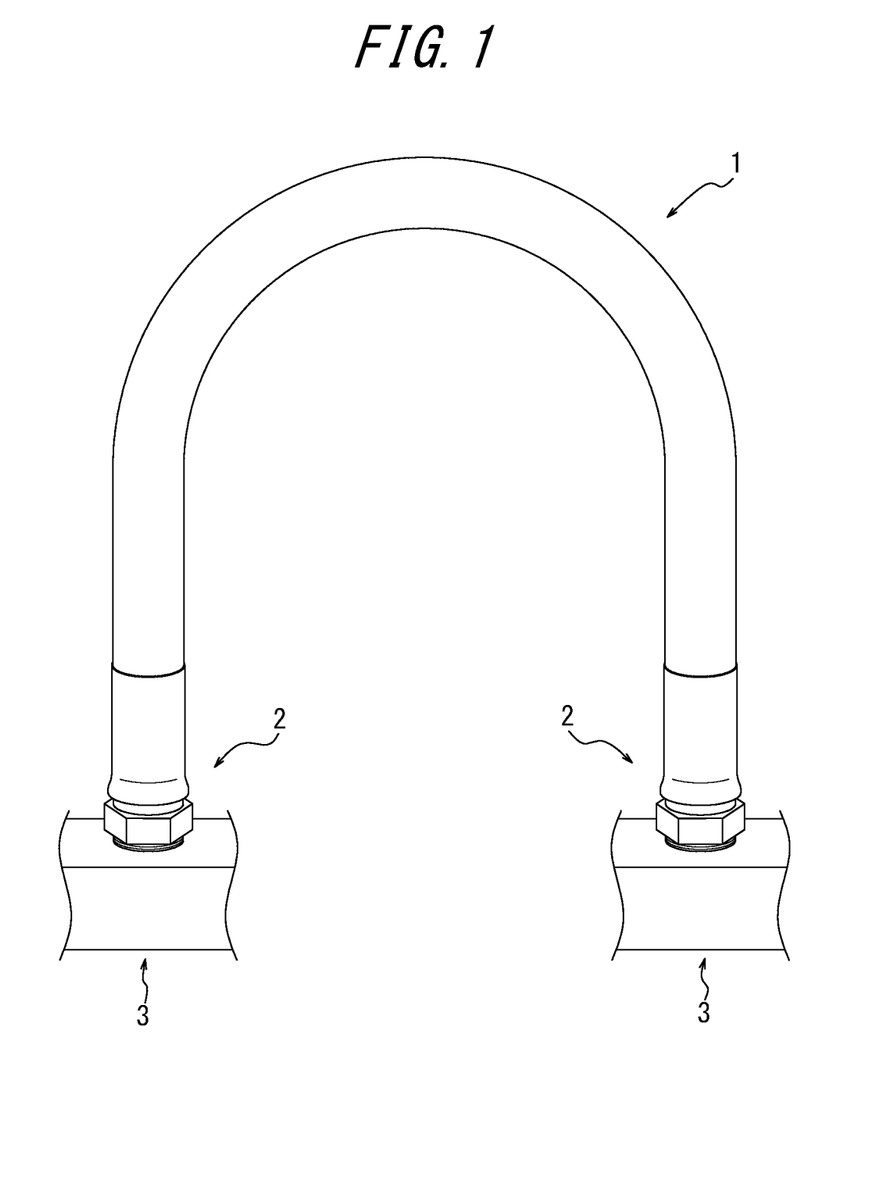
FIG. 1 is a perspective view showing the hose in a state attached to the hydraulic driving device.
Figure 2A:
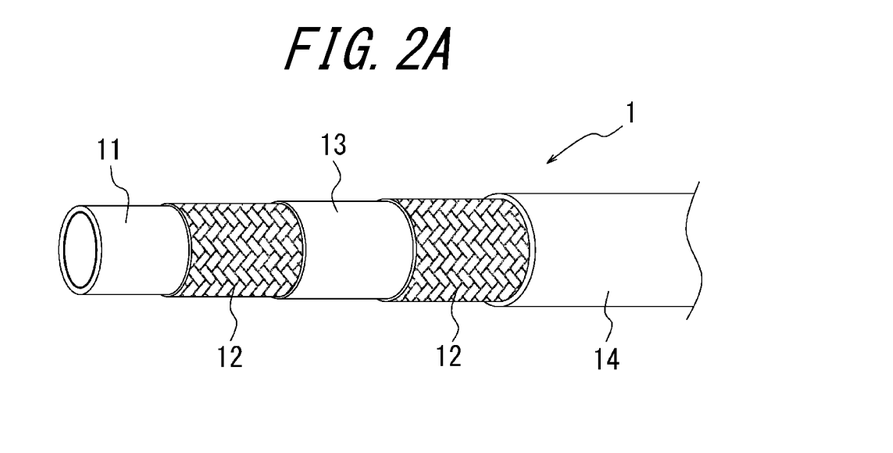
FIGS. 2A and 2B are partially exploded perspective views showing two examples of the internal structure of the hose.
Figure 2B:
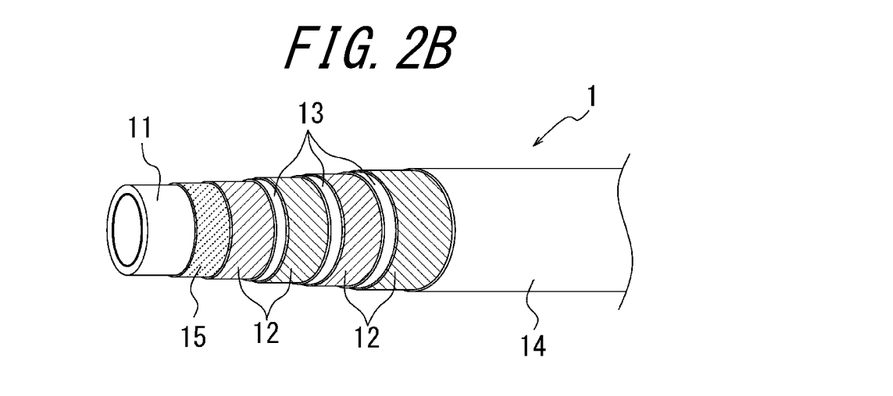

First, with reference to FIGS. 1, 2A and 2B, a hose that enables use of the method for predicting the remaining life of a hose and the method for diagnosing the deterioration level of a hose according to an embodiment of the disclosure is described. As shown in FIG. 1, such hose 1 is mounted on construction machines, plant facilities and the like (a hydraulic driving device 3 in the example of FIG. 1), and is used, for example, for transmitting a high-temperature, high-pressure fluid (oil and the like). In the example shown in FIG. 1, joints 2 are fixed on both ends of a hose 1, and the hose 1 is mounted on a hydraulic driving device 3 due to the connection of the joint 2 to the hydraulic driving device 3 by screwing. When fixing both ends of the hose 1 on the joints 2, a hose end is interposed between a core metal portion (not shown) of the joint 2 and a clamp portion (not shown) of the joint 2 disposed on the outer peripheral side of the core metal portion, and in that state, the clamp portion is fixed by caulking or the like.

As described next with reference to FIGS. 2A and 2B, the hose 1 has, at least, a metal wire layer 12 and an inner tube rubber layer 11 disposed on the inner peripheral side of the metal wire layer 12. FIGS. 2A and 2B show two examples of the internal structure of the hose 1. As shown in FIG. 2A and FIG. 2B as respective examples, the hose 1 is constituted by stacking the inner tube rubber layer 11, metal wire layer 12, intermediate rubber layer 13, and outer cover rubber layer 14 each in the radial direction.

The inner tube rubber layer 11 is a rubber layer on the innermost peripheral side, which has air tightness, heat resistance and other resistance to the fluid flowing inside it.

The metal wire layer 12 is provided as a single layer or a plurality of layers (two layers in the example of FIG. 2A and four layers in the example of FIG. 2B) and serves as a reinforcement layer for securing pressure resistance of the hose 1. The metal wire layer 12 is formed by winding a metal wire in a spiral form, a braided form or the like (braided form in the example of FIG. 2A and spiral form in the example of FIG. 2B) around the outer peripheral surface of the inner tube rubber layer 11 or on the outer peripheral side thereof. As in the example of FIG. 2B, a reinforcing fiber layer 15 formed by braiding reinforcing fibers such as an organic fiber may be provided between the inner tube rubber layer 11 and the metal wire layer 12 on the outer peripheral side thereof to prevent the metal wire constituting the metal wire layer 12 from biting into the inner tube rubber layer 11.

The intermediate rubber layer 13 is a rubber layer between the inner tube rubber layer 11 and the outer cover rubber layer 14, and when the hose has a plurality of metal wire layers 12 as in the examples of FIGS. 2A and 2B, the intermediate rubber layer 13 is positioned between the metal wire layers 12 to prevent the metal wire layers 12 from being deviated from each other and to prevent the metal wire layers 12 from contacting each other and wearing. The intermediate rubber layer 13 does not have to be provided.

The outer cover rubber layer 14 is a rubber layer on the outermost peripheral side which has wear resistance, weather resistance and the like, and is formed with rubber capable of protecting the hose 1 from the external environment.

The diameter of the hose 1 is, for example, 5 mm to 80 mm.

For the hose 1, although omitted in the drawing, the outer peripheral side of the outer cover rubber layer 14 may be coated with a protective cover (exterior protecting component) made of vinyl, metal or the like to increase protection from heat, external wounds and the like. In this case, the protective cover does not have to be adhered to the outer cover rubber layer 14.

The process of achieving the method for predicting the remaining life of a hose and the method for diagnosing the deterioration level of a hose described herein is described below.

Generally, in the hose 1 mentioned above, the rubber layer on the inner peripheral side which is particularly susceptible to the heat of the fluid inside the hose 1 (the inner tube rubber layer 11 and intermediate rubber layer 13, and particularly, the inner tube rubber layer 11) is gradually hardened by thermal aging as the total usage time increases due to long term use. Hardening of the inner tube rubber layer 11 may cause a decrease in the degree of adhesion (surface pressure) of the inner tube rubber layer 11 to the joint 2 and lead to leakage of the fluid inside the hose 1. To prevent the use of the hose 1 in a state where the inner tube rubber layer 11 is excessively thermally aged and thus hardened, it would be most ideal to measure the hardness of the inner tube rubber layer 11 itself on a regular basis without breaking the hose 1. However, a method enabling such measurement has not been established. For example, even if the hardness is measured using a durometer hardness meter by pressing the hose 1 from outside, there are problems in that the hardness of the metal wire layer 12 which is not affected by the heat is measured or that measurement of hoses with protective covers cannot be carried out. Further, in some cases, only the hardness of the outer cover rubber layer 14 where, due to the external environment, the degree of deterioration may be different from the rubber layer on the inner peripheral side is obtained as the measurement results, and accurate measurement of the deterioration is difficult.

We made further studies and focused on the fact that, as the rubber layers 11 and 13 on the inner peripheral side are hardened by thermal aging, the movement of the metal wire layer 12 adjacent to the rubber layers 11 and 13 on the inner peripheral side in the radial direction is limited and as a result, it becomes difficult to bend the hose 1 itself. Even when the hose 1 is not provided with an intermediate rubber layer 13, it becomes difficult to bend the hose 1 in accordance with the use thereof. This is thought to be because, in the manufacturing process of the hose (i.e. forming a metal wire layer 12 on the outer peripheral side of the inner tube rubber layer 11, and then vulcanizing), the inner tube rubber layer 11 moves toward the inside of the metal wire layer 12 adjacent to its outer peripheral side and therefore, the inner tube rubber layer 11 is hardened there via use of the hose, such that the movement of the metal wire layer 12 becomes limited. Further, we came to think that, by quantifying the difficulty of bending the hose 1, it would be possible to easily carry out prediction of the remaining life and diagnosis of the deterioration level of the hose 1 without breaking the hose 1. The disclosure has been completed based on these findings.

For the hose subject to remaining life prediction or deterioration diagnosis, a hose bending test is performed (testing step), and using the test results of the hose bending test, remaining life prediction or deterioration diagnosis of the hose is performed (predicting step or diagnosing step).

First, an example of a hose bending test performed in the disclosure is described.

(Hose Bending Test)

Figure 3:
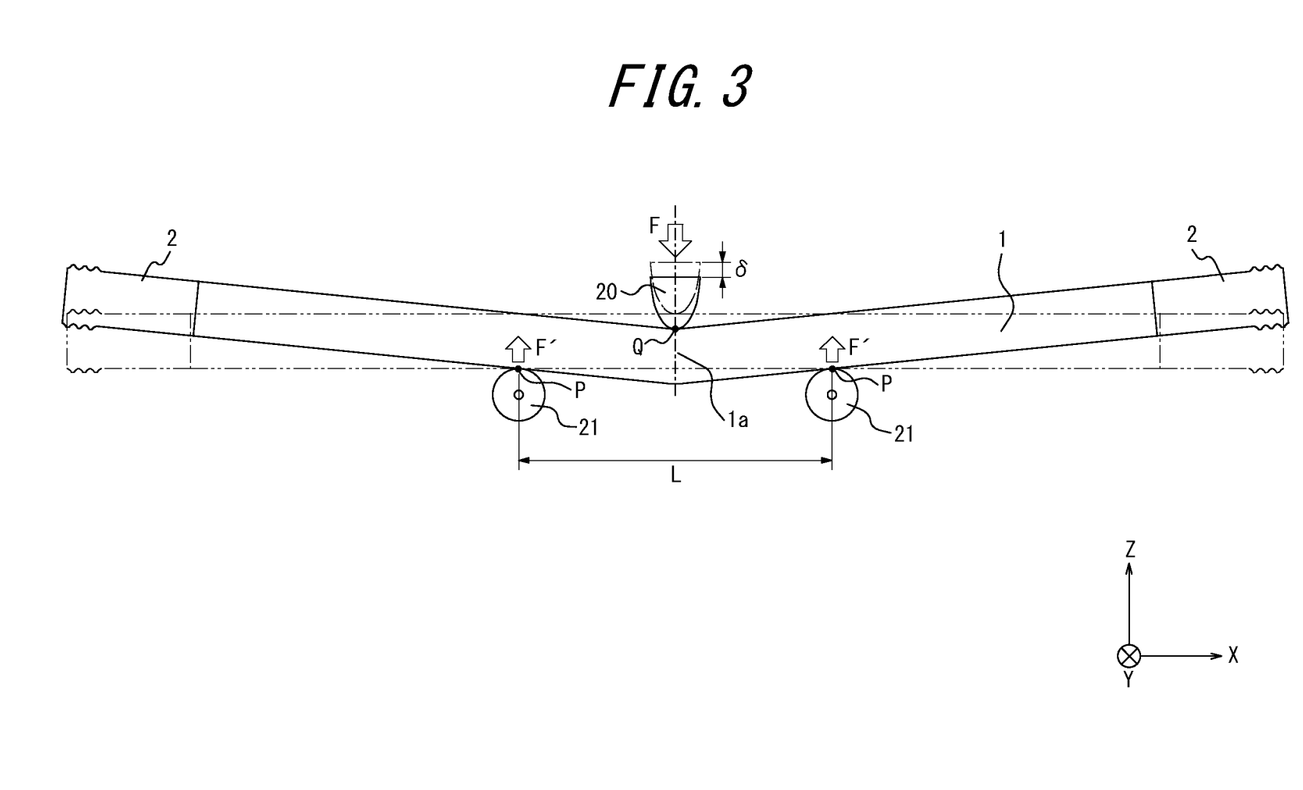
FIG. 3 describes an example of the hose bending test performed in the method for predicting the remaining life of a hose and the method for diagnosing the deterioration level of the hose described herein.
Figure 4:
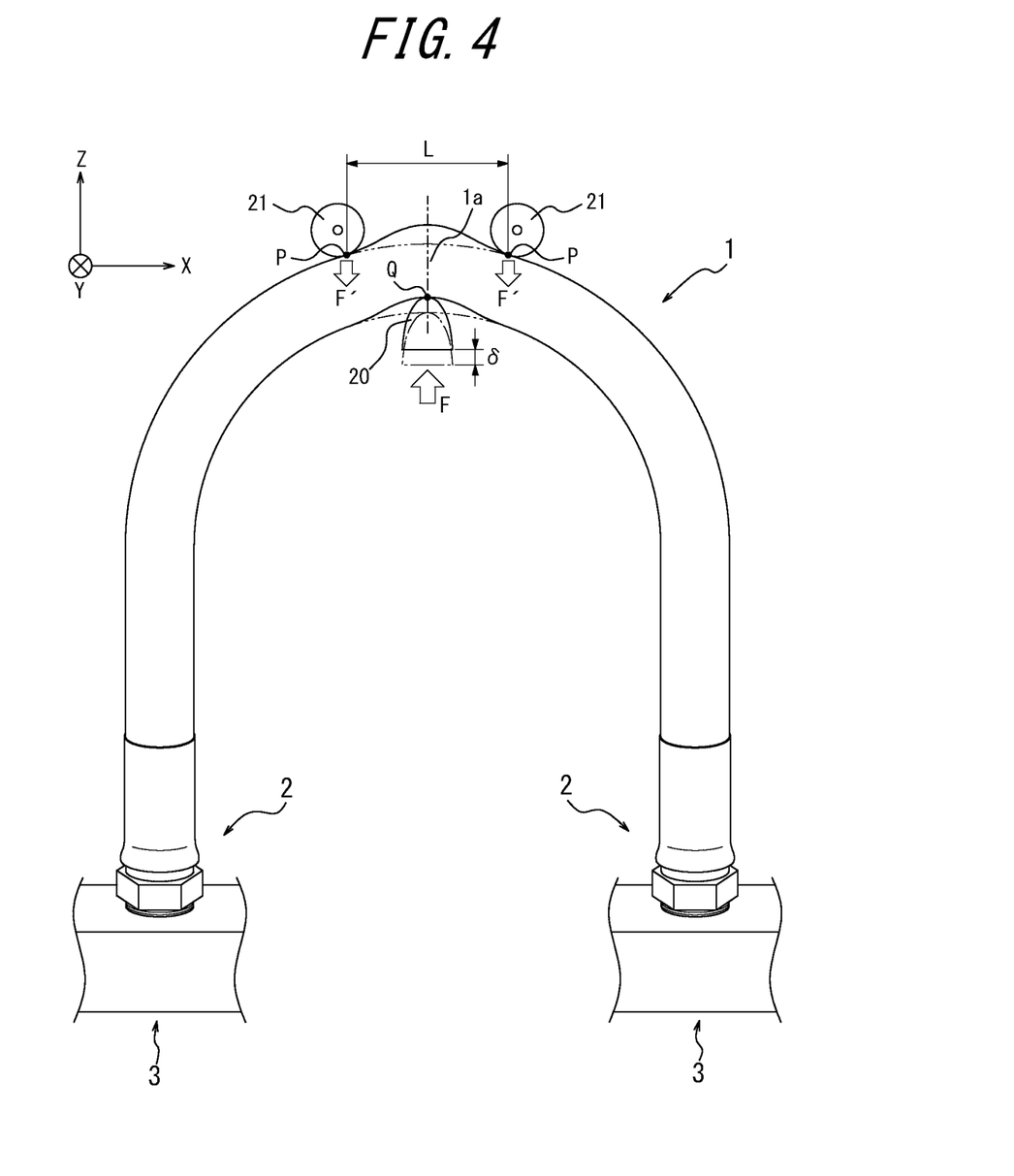
FIG. 4 describes another example of the hose bending test performed in the method for predicting the remaining life of a hose and the method for diagnosing the deterioration level of the hose described herein.

FIGS. 3 and 4 describe different examples of methods for carrying out the hose bending test. For convenience of explanation, the right-left direction, front-back direction, and up-down direction as seen in FIGS. 3 and 4 are respectively referred to as X-axis direction, Y-axis direction and Z-axis direction. The X-axis, Y-axis and Z-axis are perpendicular to each other. The up-down direction as seen in FIGS. 3 and 4 is not limited to the actual vertical direction, and may be another direction in real (e.g. direction along the horizontal plane in real).

In the example of FIG. 3, a three point bending test is performed with the hose 1 removed from the hydraulic driving device 3. First, the joints 2 on both ends of the hose 1 are removed from the hydraulic driving device 3, and with the joints 2 fixed on both ends of the hose 1, the hose 1 is straightened and placed on a supporting means 21. The supporting means 21 is in contact with the hose 1 at the two supporting positions P (fulcrums) separated from each other along the extending direction of the hose 1. Here, the distance between the supporting positions P (i.e. the length of the line connecting the supporting positions P) is L.

At this state, an external force F is exerted, by an external force exerting means 20, on a hose portion 1a located approximately on an equidistant line from the pair of supporting positions P to press the hose 1, from a position Q (point of action) on the opposite side of the supporting positions P in the radial direction (Z-axis positive side). While the external force F is exerted on the hose portion 1a, the supporting means 21 supports the hose 1 from a direction opposite to the direction of the external force F at supporting positions P on both sides of the hose portion 1a in the extending direction of the hose 1. Here, "supports the hose 1 from the direction opposite to the direction of the external force F" means that resistance F' which will be exerted on the hose 1 by the supporting means 21 at the supporting positions P includes a component in the direction that is opposite to the direction of the external force F. Further, while the action of this external force F causes bending deformation in the hose portion 1a, the hose portion 1a is displaced in the direction of the external force F. The hose 1 has a metal wire layer 12 and therefore, when the external force F is exerted from one side of the radial direction of the hose 1 (Z-axis positive side) to the Z-axis negative direction as in the example of FIG. 3, the hose portion 1a is not deformed such that the surrounding walls of one side of the radial direction (Z-axis positive side) moves toward the surrounding walls of the other side of the radial direction (Z-axis negative side), in other words, in a manner that the hose portion 1a is crushed, but rather, the surrounding walls of the entire circumference is displaced against the supporting positions P in the direction of the external force F to cause bending deformation.

For example, the hose portion 1a is displaced in the direction of the external force F by a predetermined displacement amount δ, the external force F required for the displacement is measured, and the value of the measured external force F is obtained as the test result. That is, for a plurality of hoses 1 to be tested, the same displacement amount δ is used to perform the hose bending tests, and the measurement values of the external forces F for each hose is obtained as the test results. In this case, remaining life prediction or deterioration diagnosis of the hose is performed based on the comparison results of the measurement values of the external forces F obtained using the same displacement amount δ.

An alternative is to exert an external force F of a predetermined magnitude on the hose portion 1a, measure the displacement amount δ of the hose portion 1a in the direction of the external force F, and use the value of the measured displacement amount δ as the test result. That is, for a plurality of hoses 1 to be tested, an external force F of the same magnitude is used to perform hose bending tests, and the measurement values of the displacement amounts δ are obtained as the test results. In this case, remaining life prediction or deterioration diagnosis of the hose is performed based on the comparison results of the measurement values of the displacement amounts δ obtained using the external force F of the same magnitude.

In the example of FIG. 4, a three point bending test is performed with the hose 1 attached to the hydraulic driving device 3. For the hose bending test of this example, parts different from the example of FIG. 3 will mainly be described below. In the example of FIG. 4, the hose 1 is attached to the hydraulic driving test 3 in state that the hose is curved in a convex U-shaped toward the Z-axis positive side. First, the supporting means 21 are placed on the hose 1. Here, the supporting means 21 is in contact with the hose 1 at the two supporting positions P (fulcrums) separated from each other along the extending direction of the hose 1. In the example of FIG. 4, the equidistant line from the pair of supporting positions P passes through the center of the hose 1 in the extending direction of the hose 1, yet this example is not limiting, and each supporting position P can be disposed so that the equidistant line from the pair of supporting positions P passes through an arbitrary position of the hose 1 in the extending direction of the hose 1.

At this state, an external force F is exerted, by an external force exerting means 20, on a hose portion 1a located on the equidistant line from the pair of supporting positions P to press the hose 1 from the position Q (point of action) on the opposite side of the supporting positions P in the radial direction. While the external force F is exerted on the hose portion 1a, the supporting means 21 supports the hose 1 from the direction opposite to the direction of external force F (Z-axis positive direction) at supporting positions P on both sides of the hose portion 1a in the extending direction of the hose 1. Further, while the action of this external force F causes bending deformation in the hose portion 1a, the hose portion 1a is displaced in the direction of the external force F.

Further, as in the example of FIG. 3, while the external force F is exerted on the hose portion 1a to cause bending deformation in the hose portion 1a, the external force F required to displace the hose portion 1a in the direction of the external force F by a predetermined displacement amount δ, or the displacement amount δ in the direction of the external force F of the hose portion 1a when the external force F of a predetermined magnitude is exerted on the hose portion 1a is obtained as the test result.

As described above, in the above example of the hose bending test performed in the disclosure, the hose 1 does not have to be broken, and the user can easily perform the test at the use site of the hose 1. Further, as in the example of FIG. 4, the hose bending test can be performed with the hose 1 mounted on the hydraulic driving device 3 or the like, and in such case, the convenience for the user is further improved.

In the examples of FIGS. 3 and 4, while the external force F is exerted on the hose portion 1a, three point bending is performed where the supporting means 21 supports the hose 1 from the direction opposite to the direction of the external force F at the supporting positions P on both sides of the hose portion 1a in the extending direction of the hose 1, and thus, compared to two point bending or four point bending, the degree of bending deformation at the hose portion 1a becomes larger. Therefore, the difference in the test results according to the deterioration level of the hose 1 appears more clearly. As a result, the accuracy of remaining life prediction or deterioration diagnosis of the hose is improved.

The hose bending test performed in the disclosure is, however, not limited to three point bending, and as long as it is a testing method where an external force F is exerted on one or more hose portions 1a, and while causing bending deformation in the hose portion 1a, the hose portion 1a can be displaced in the direction of the external force F, any method such as four point bending, two point bending, and one point bending can be adopted to perform the hose bending test. In the case of one point bending, the supporting positions P (fulcrum) and supporting means 21 are not required.

Further, in the hose bending test performed in the disclosure, the test can be performed with sufficient accuracy even if the hose 1 is coated with the aforementioned protective cover (exterior protecting component), and therefore the convenience for the user is improved.

In the example of the above mentioned hose bending test performed in the disclosure, the distance L between the supporting positions P is preferably 150 mm or less. This way, for example, when obtaining the external force F as a test result by fixing the displacement amount δ of the hose portion 1a, the displacement amount δ can be made sufficiently small, and therefore the user can easily perform the hose bending test. Further, this way, even if the hose 1 is mounted on the hydraulic driving device 3 or the like in a bent state, the small distance between the supporting positions P will enable the portion between the supporting positions P to be regarded as extending in a straight line, and therefore the hose bending test can be easily performed with the hose 1 attached to the hydraulic driving device 3 or the like.

In the hose bending test performed in the disclosure, for example, provided that the displacement amount δ of the hose portion 1a is fixed and the external force F is obtained as the test result, the difference in the test results according to the deterioration level of the hose 1 appears sufficiently clearly even if the displacement amount δ of the hose portion 1a in the direction of the external force F is a minute amount of 20 mm or less. In this case, it is not necessary to largely bend the hose 1, and therefore the user can easily perform the hose bending test and suppress the load on the hose 1. Although, the displacement amount δ is not particularly limited, and may be adjusted as appropriate depending on the conditions of the diameter and the like of the hose, a displacement amount of 0.1 mm or more is preferable. With this range, test results can easily be obtained at a sufficient accuracy.

In the examples of FIGS. 3 and 4, the external force F is exerted on the hose portion 1a to press the hose 1, from the position Q on the opposite side of the supporting positions P in the radial direction. Alternatively or additionally, the external force F can be exerted to pull the hose 1, from the position of the hose portion 1a on the same side as the fulcrum positions P in the radial direction. Even in this case, while the external force F is exerted on the hose portion 1a, the supporting means 21 supports the hose 1 from the direction opposite to the direction of the external force F at the supporting positions P on both sides of the hose portion 1a in the extending direction of the hose 1.

Further, in the hose bending test, the supporting means 21 may be composed of a roller that is rotatable in accordance with the bending deformation of the hose portion 1a while contacting with the hose 1 at the supporting positions P. This way, the frictional force between the hose 1 and the supporting means 21 can be reduced while the bending deformation is formed in the hose portion 1a, and therefore the user can perform the hose bending test more smoothly.

Further, even if the hose 1 is coated with the aforementioned protective cover (exterior protecting component), the hose bending test can be performed with sufficient accuracy, and therefore the convenience for the user is improved.

The remaining life prediction and deterioration diagnosis of the hose according to an embodiment of the disclosure using the test results of the hose bending test are described below.

(Remaining Life Prediction of Hose)

In the remaining life prediction of the hose, the remaining life of the hose subject to prediction is predicted based on the comparison between the test result of the hose bending test obtained from a hose subject to remaining life prediction and the test result obtained by performing a hose bending test beforehand for a hose of the same type (same diameter, internal structure and the like) which is in a use limit state (hereinafter, also referred to as "hose subject to comparison") under the same or relatively close testing conditions (Predicting step). The remaining life refers to the remaining use time until the hose 1 reaches the use limit state. The degree of deterioration of the hose 1 to be determined as the use limit state (depleted state) may be set as appropriate in accordance with requests.

Testing conditions for the hose bending test include, for example, the distance L between the supporting positions. Further, when the displacement amount δ is fixed and the external force F is obtained as the test result, the displacement amount δ is also a testing condition. Alternatively, when the external force F is fixed and the displacement amount δ is obtained as the test result, the external force F is also a testing condition.

As the method of predicting the remaining life based on the comparison between the test results for the hose subject to prediction and the hose subject to comparison, any method can be used. For example, by performing hose bending tests beforehand under the same condition for a plurality of hoses of the same type with different total usage time, tendency data showing the relation between the total usage time and the test result of the hose bending test is obtained. It is preferable to store such tendency data for a plurality of types of hoses and testing conditions. Further, in the predicting step, tendency data, from among the stored data, in which the type of hose is the same as the hose subject to prediction and the testing conditions are the same as or relatively close to the test performed for the hose subject to prediction is used, and based on the comparison between the test result of the hose subject to prediction and the test result of the hose subject to comparison which is in a use limit state, the remaining life of the hose subject to prediction is predicted. Here, for example, the use time predicted to be required for the test result to change from the value obtained for the hose subject to prediction to the value for the hose subject to comparison which is in a use limit state may be obtained by extrapolation based on tendency data, and this may be used as the remaining life of the hose subject to prediction.

Further, by taking into consideration of the temperature of the fluid inside the hose 1 in addition to the total usage time, the prediction accuracy is further improved.

(Deterioration Diagnosis of Hose)

In the deterioration diagnosis of the hose, the deterioration level of the hose subject to diagnosis is diagnosed based on the comparison between the test result of the hose bending test obtained from a hose subject to deterioration diagnosis and the test result obtained by performing a hose bending test beforehand for a hose of the same type (same diameter, internal structure and the like) as the hose subject to diagnosis and of a known total usage time (hose subject to comparison) under the same or relatively close testing conditions (Diagnosing step).

As a method of diagnosing the deterioration based on the comparison between the test results for the hose subject to diagnosis and the hose subject to comparison, any method can be used. For example, first, as described in relation to remaining life prediction, tendency data between the total usage time and the test results, in which the type of hose is the same as the hose subject to diagnosis and the testing conditions are the same as or relatively close to the test performed for the hose subject to diagnosis is used to obtain the test result for the hose subject to comparison with less total usage time than the hose subject to diagnosis. Further, based on the comparison between the test result of the hose subject to diagnosis and the test result of the hose subject to comparison with less total usage time than the hose subject to diagnosis, the deterioration level of the hose subject to diagnosis is diagnosed. Here, for example, the ratio of the test result of the hose subject to diagnosis to the test result of the hose subject to comparison with less total usage time than the hose subject to diagnosis may be used as the deterioration level of the hose subject to diagnosis.

INDUSTRIAL APPLICABILITY

The method for predicting the remaining life of the hose and the method for diagnosing the deterioration level of the hose described herein can be used for, for example, hoses used in construction machines, plant facilities and the like.

REFERENCE SIGNS LIST

1: Hose
1a: Hose portion
2: Joint
3: Hydraulic driving device
11: Inner tube rubber layer
12: Metal wire layer
13: Intermediate rubber layer
14: Outer cover rubber layer
15: Reinforcing fiber layer
20: External force exerting means
21: Supporting means
P: Supporting position (fulcrum)
Q: Point of action

The invention claimed is:

1. A method for predicting remaining life of a hose having a metal wire layer and an inner tube rubber layer disposed on an inner peripheral side of the metal wire layer, the method comprising:

a testing step of performing a hose bending test on a hose subject to prediction for remaining life; and a predicting step of predicting remaining life of the hose subject to prediction based on comparison between a test result obtained by performing the hose bending test on the hose subject to prediction and a test result obtained by performing the hose bending test beforehand on a hose of the same type which is in a use limit state, wherein during the hose bending test, while an external force is exerted on a predetermined hose portion of a hose subject to testing to cause bending deformation in the hose portion, either a value of the external force required to displace the hose portion in a direction of the external force by a predetermined displacement amount, or a value of a displacement amount in a direction of the external force of the hose portion of when the external force of a predetermined magnitude is exerted on the hose portion is measured, and the measured value is obtained as the test result, and wherein:

the remaining life refers to a remaining use time until the hose reaches the use limit state in which a predetermined degree of thermal aging of the inner tube rubber layer has occurred to the hose, the predetermined displacement amount is 0.1 to 20 mm, and the value of the external force required to displace the hose portion in the direction of the external force by the predetermined displacement amount increases as the bending stiffness of the hose increases due to thermal aging of the inner tube rubber layer.

2. The method for predicting remaining life of a hose according to claim 1, wherein, during the hose bending test, while exerting the external force on the hose portion, the hose is supported from a direction opposite to the direction of the external force at predetermined supporting positions on both sides of the hose portion in an extending direction of the hose.

3. The method for predicting remaining life of a hose according to claim 2, wherein a distance between the predetermined supporting positions is 150 mm or less.

4. The method for predicting remaining life of a hose according to claim 1, wherein the hose has an outermost layer coated with a protective cover.

5. The method for predicting remaining life of a hose according to claim 1, wherein, during the predicting step, tendency data is used for the predicting, wherein the tendency data is obtained by performing hose bending tests beforehand under the same condition for a plurality of hoses of the same type with different total usage time and shows a relation between the total usage time and the test result of the hose bending tests.

6. The method for predicting remaining life of a hose according to claim 1, wherein the bending test is performed with both ends of the hose being fixed.

7. A method for diagnosing deterioration level of a hose having a metal wire layer and an inner tube rubber layer disposed on an inner peripheral side of the metal wire layer, the method comprising:

a testing step of performing a hose bending test on a hose subject to diagnosis for deterioration level; and a diagnosing step of diagnosing deterioration level of the hose subject to diagnosis based on comparison between a test result obtained by performing the hose bending test on the hose subject to diagnosis and a test result obtained by performing the hose bending test beforehand on a hose of the same type as the hose subject to diagnosis and of a known total usage time, wherein during the hose bending test, while an external force is exerted on a predetermined hose portion of a hose subject to testing to cause bending deformation in the hose portion, either a value of the external force required to displace the hose portion in a direction of the external force by a predetermined displacement amount, or a value of the displacement amount in a direction of the external force of the hose portion of when the external force of a predetermined magnitude is exerted on the hose portion is measured, and the measured value is obtained as the test result, wherein:

the deterioration of the hose is caused by thermal aging of the inner tube rubber layer of the hose, the predetermined displacement amount is 0.1 to 20 mm, and the value of the external force required to displace the hose portion in the direction of the external force by the predetermined displacement amount increases as the bending stiffness of the hose increases due to thermal aging of the inner tube rubber layer.

8. The method for diagnosing deterioration level of a hose according to claim 7, wherein, during the hose bending test, while exerting the external force on the hose portion, the hose is supported from a direction opposite to the direction of the external force at predetermined supporting positions on both sides of the hose portion in an extending direction of the hose.

9. The method for diagnosing deterioration level of a hose according to claim 8, wherein a distance between the predetermined supporting positions is 150 mm or less.

10. The method for diagnosing deterioration level of a hose according to claim 7, wherein the hose has an outermost layer coated with a protective cover.

11. The method for diagnosing deterioration level of a hose according to claim 7, wherein, during the diagnosing step, a ratio of the test result of the hose subject to diagnosis to the test result of the hose of the known total usage time is used as the deterioration level of the hose subject to diagnosis.

12. The method for diagnosing deterioration level of a hose according to claim 7, wherein the bending test is performed with both ends of the hose being fixed.

* * * * *